United States Patent [19]

Alt et al.

[11] Patent Number: 6,162,884
[45] Date of Patent: Dec. 19, 2000

[54] OLEFIN OLIGOMERIZATION AND PROCESSES THEREOF

[75] Inventors: Helmut G. Alt; Alexander Köppl, both of Bayreuth, Germany

[73] Assignee: Phillips Petroleum Company, Bartlesville, Okla.

[21] Appl. No.: 09/302,133

[22] Filed: Apr. 29, 1999

Related U.S. Application Data

[62] Division of application No. 09/050,725, Mar. 30, 1998, Pat. No. 5,932,670.

[51] Int. Cl.[7] .................................................... C08F 4/602
[52] U.S. Cl. ...................... 526/161; 526/352; 526/348; 526/135; 526/147; 526/171; 526/172; 502/117; 502/123; 502/155
[58] Field of Search ................................. 526/161, 352, 526/135, 147, 171, 172, 348; 502/117, 123, 155

[56] References Cited

U.S. PATENT DOCUMENTS

| | | | |
|---|---|---|---|
| 5,283,278 | 2/1994 | Dair et al. ............................... | 524/399 |
| 5,461,126 | 10/1995 | Knudsen et al. ........................... | 526/96 |
| 5,557,023 | 9/1996 | Somogyvari et al. .................... | 585/513 |
| 5,707,913 | 1/1998 | Schlund et al. ........................... | 502/117 |
| 5,714,556 | 2/1998 | Johnson et al. ........................... | 526/135 |
| 5,817,724 | 10/1998 | Aoki et al. ............................... | 526/160 |
| 5,852,145 | 12/1998 | McLain et al. ........................... | 526/161 |
| 5,866,663 | 2/1999 | Brookhart et al. ....................... | 526/161 |

FOREIGN PATENT DOCUMENTS

WO 96/23010  8/1996  WIPO .

OTHER PUBLICATIONS

Crociani et al., Organometallics, vol. 16, pp. 384–391, 1997.

*Primary Examiner*—David W. Wu
*Assistant Examiner*—Ling-Siu Choi
*Attorney, Agent, or Firm*—Lynda S. Jolly

[57] ABSTRACT

Novel catalyst systems which comprise 2-pyridine carboxaldimine nickel dihalide complexes can be used with an organoaluminum cocatalyst in slurry oligomerization or polymerization processes to oligomerize or polymerize mono-1-olefins and, optionally a higher alpha-olefin comonomer, to produce low molecular weight polymers or synthetic oils.

15 Claims, No Drawings

OLEFIN OLIGOMERIZATION AND PROCESSES THEREOF

This application is a Division of application Ser. No. 09/050,725, filed Mar. 30, 1998, now U.S. Pat. No. 5,932,670.

BACKGROUND

This invention relates to oligomerization and homopolymerization of mono-1-olefin monomers, such as ethylene and propylene, and copolymerization of a mono-1-olefin monomers, such as ethylene and propylene, with at least one higher alpha-olefin comonomer.

It is well known that mono-1-olefins, such as ethylene and propylene, can be oligomerized and polymerized with catalyst systems employing transition metals such as titanium, vanadium, chromium, nickel and/or other metals, either unsupported or on a support such as alumina, silica, titania, and other refractory metals. Supported polymerization catalyst systems frequently are used with a cocatalyst, such as alkyl boron and/or alkyl aluminum compounds. Organometallic catalyst systems, i.e., Ziegler-Natta-type catalyst systems usually are unsupported and frequently are used with a cocatalyst, such as methylaluminoxane.

It is also well-known that, while no oligomer or polymer production process is easy, slurry, or loop, oligomerization or polymerization processes are relatively much more commercially desirable than other oligomerization or polymerization processes. Furthermore, the type of oligomerization or polymerization process used can have an effect on the resultant polymer. For example, higher reactor temperatures can result in low catalyst activity and productivity, as well as a lower molecular weight oligomer or polymer product. Higher reactor pressures also can decrease the amount of desirable branching in the resultant oligomer or polymer.

Most oligomer or polymer products made in slurry processes, especially those oligomer or polymer products made using supported chromium catalyst systems, have a broader molecular weight distribution and, therefore, the oligomer or polymer product is much easier to process into a final product. Oligomers or polymers made by other processes, such as, for example, higher temperature and/or higher pressure solution processes, can produce oligomers or polymers having a narrow molecular weight distribution; these oligomers or polymers can be much more difficult to process into an article of manufacture.

Unfortunately, many homogeneous organometallic catalyst systems have low activity, high consumption of very costly cocatalysts, like supported organoaluminum compounds or methylaluminoxane (MAO), and can produce low molecular weight oligomers or polymers with a narrow molecular weight distribution. Furthermore, even though MAO can be necessary to produce an oligomer or polymer with desired characteristics, an excess of MAO can result in decreased catalyst system activity. Additionally, these types of homogeneous catalyst systems preferably are used only in solution or gas phase oligomerization or polymerization processes.

SUMMARY OF THE INVENTION

It is an object of this invention to provide novel catalyst systems useful for oligomerization or polymerization.

It is another object of this invention to provide catalyst systems which are relatively simple to make, have increased activity and increased productivity.

It is a further object of this invention to provide catalyst systems which have reduced cocatalyst consumption.

It is still another object of this invention to provide improved oligomerization or polymerization processes.

It is yet another object of this invention to provide oligomers, homopolymers of mono-1-olefins and copolymers of at least two different mono-1-olefin(s) that can be processed easily, as indicated by increased branching and a broad molecular weight distribution.

It is still another object of this invention to provide oligomers, homopolymers of mono-1-olefins and copolymers of at least two different mono-1-olefin(s) that have decreased molecular weight.

It is still a further object of this invention to provide oligomers of one or more mono-1-olefins that have applicability as synthetic oils.

In accordance with this invention catalyst systems comprising 2-pyridine carboxaldimine nickel dihalide complexes which comprise two halogen ligands selected from the group consisting of fluorine, chlorine, bromine, iodine and mixtures thereof and an organoaluminum cocatalyst system are provided. Processes to make these catalyst systems also are provided.

In accordance with another embodiment of this invention, slurry oligomerization or polymerization processes comprising contacting ethylene, and optionally one or more higher alpha-olefins, in a reaction zone with catalyst systems comprising 2-pyridinecarboxaldimine nickel dihalide complexes which comprise two halogen ligands selected from the group consisting of fluorine, chlorine, bromine, iodine and mixtures thereof in the presence of an organoaluminum cocatalyst system are provided.

In accordance with yet another embodiment of this invention, oligomers, homopolymers of ethylene and copolymers of ethylene and one or more higher alpha-olefins which can be characterized as having low molecular weight and increased branching are provided.

DESCRIPTION OF THE PREFERRED EMBODIMENTS

Catalyst Systems

Catalyst systems of this invention can be characterized as 2-pyridinecarboxaldimine nickel dihalide complexes comprising two halogen ligands selected from the group consisting of fluorine, chlorine, bromine, iodine and mixtures thereof having a general formula as shown below in Compound I,

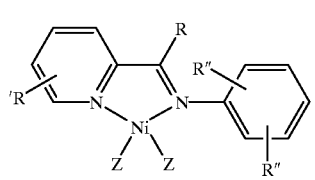

Compound I wherein R' and R" can be the same or different and are selected from the group consisting of branched and/or linear alkyl or aromatic groups having from about 1 to about 15, preferably from about 1 to about 12, carbon atoms per alkyl group and R' or R" can be in any position on the aromatic ring; and R can be the same or different and is selected from the group consisting of hydrogen and linear, branched, cyclic, bridging, aromatic, and/or aliphatic hydrocarbons, having from about 1 to about 70 carbon atoms per radical group.

R' and R" substituents on the aromatic and pyridine rings of the 2-pyridinecarboxaldimine nickel dihalide complex can be the same or different, and are selected from the group consisting of hydrogen and branched or linear, aliphatic or aromatic groups having from about 1 to about 15 carbon atoms per alkyl group. R' and R" groups having more than about 15 carbon atoms per group can result in a catalyst system with lower activity and/or productivity. While not wishing to be bound by theory, it is believed that larger substituent groups can cause steric hindrance in the catalyst system, thereby which can decrease catalyst system activity and/or productivity. Exemplary alkyl substituents are selected from the group consisting of methyl, ethyl, propyl, isopropyl, butyl, isobutyl, tert-butyl, phenyl groups, fused phenyl groups (such that the pyridine group and the substituent taken together form a quinoline group), and mixtures of two or more thereof. Preferably, the R' or R" substituent is an electron-donating species, selected from the group consisting of linear or branched aliphatic or fused aromatic groups having from about 1 to about 15 carbon atoms per group. Most preferably, the R" groups are both the same and are selected from the group consisting of methyl and isopropyl and the R' group is selected from the group consisting of hydrogen, methyl, or fused phenyl, due to commercial availability and ease of synthesis of the ligand.

The R' and R" groups can be in any position, i.e., from 2 to 6, on the aromatic ring. Preferably, the R' group is either in the 2 and/or 6 position, due to ease of synthesis. Most preferably, for best catalytic activity and productivity, the R' group is on the 2 position on the aromatic ring. Preferably, the R" groups, which can be the same or different, are either in the 2 and/or 6 position, due to ease of synthesis. Most preferably, for best catalytic activity and productivity, both R" groups are the same and are in the 2 and 6 positions on the aromatic ring.

The R substituent is selected from the group consisting of hydrogen and branched, linear, cyclic, aromatic or aliphatic radicals having from about 1 to about 70 carbon atoms per radical. Further, the R substituent can be linked, or joined, to the pyridine group to form a ring. While not wishing to be bound by theory, it is believed that radicals having more than 70 carbon atoms can add to the steric hindrance of the catalyst systems and hinder catalyst activity and productivity. Preferably, the R substituent group is selected from the group consisting of hydrogen and branched, linear, cyclic, aromatic or aliphatic radicals having from about 1 to about 20 carbon atoms per radical, due to commercial availability and ease of synthesis of the ligand. Most preferably, the R substituent is terminal or is linked to the pyridine group and is selected from the group consisting of hydrogen and branched, linear, cyclic, aromatic or aliphatic radicals having from about 1 to about 12 carbon atoms per radical, for the reasons given above. Exemplary R substituents include, but are not limited to, hydrogen, methyl, ethyl, propyl, phenyl, or linked to the pyridine to form a cyclopentyl or cyclohexyl ring. Preferably, the R substituent is selected from the group consisting of hydrogen and methyl for best resultant catalyst system activity and productivity.

The Z substituent of the 2-pyridinecarboxaldimine nickel dihalide complex is a halogen selected from the group consisting of fluorine, chlorine, bromine, iodine, and mixtures thereof. Preferably, Z is selected from the group consisting of chlorine and bromine for high catalyst activity and productivity. Most preferably, the group Z is chlorine for best catalyst system activity and productivity.

Novel catalyst systems disclosed in this application can be prepared in accordance with any manner known in the art. Preparation of these novel catalyst systems does not require the presence of an oxidizing agent. Most preferably, an oxidizing agent is not present, i.e., is absent, during catalyst system preparation. In fact, while not wishing to be bound by theory, it is believed that the presence of an oxidizing agent during catalyst preparation and/or polymerization can be detrimental to either the novel catalyst system and/or the formation of a polymer product because it may cause the formation of an unstable form of the nickel complex that can decompose more easily than the parent nickel complex or the oxidizing agent may react with a cocatalyst to render the cocatalyst unreactive with the nickel complex.

The 2-pyridinecarboxaldimine nickel dihalide complex catalyst system disclosed in this application can be prepared by any method known in the art. For example, approximate molar equivalents of a 2-pyridinecarboxaldimine ligand and a nickel compound can be contacted in the presence of any compound that can dissolve both the 2-pyridinecarboxaldimine ligand and nickel compound, either partially or completely. The contacting conditions can be any conditions suitable to effect the formation of a 2-pyridinecarboxaldimine nickel dihalide complex. Preferably, for best product results, the 2-pyridinecarboxaldimine ligand/nickel complex mixture is contacted at room temperature under a dry atmosphere for any amount of time sufficient to form the 2-pyridinecarboxaldimine nickel dihalide complex. Sometimes, completion of the formation of the 2-pyridinecarboxaldimine nickel dihalide complex can be evidenced by a color change. Generally, contacting times of about 8, and preferably 12 hours are sufficient. Usually, as a result of the preparation procedure, the resultant 2-pyridinecarboxaldimine nickel dihalide complex will comprise from about 3 to about 20, preferably from about 5 to about 15, weight percent nickel, based on the total mass of the 2-pyridinecarboxaldimine nickel dihalide complex. The presence of oxygen is not thought to be detrimental to this aspect of the preparation procedure.

In general, 2-pyridinecarboxaldimine ligands are contacted with a nickel β-diketonate halide to form 2-pyridinecarboxaldimine nickel dihalide complexes. Typical syntheses of nickel dihalide complexes related to those described in this invention can be found in Matsubayashi, G., Okunanka, M., *J. Organmet. Chem.*, Vol. 56, p. 216 (1973), herein incorporated by reference. Usually, for ease of catalyst system preparation, the 2-pyridinecarboxaldimine ligand is prepared first. The catalyst preparation procedure can vary, depending on the substituents on the 2-pyridinecarboxaldimine ligand. Usually, ligands are synthesized by the condensation, i.e., refluxing, of pyridine-2-carbaldehyde or quinoline-2-carbaldehyde with an equimolar amount of an analine derivative in ethanol. If the corresponding acetyl compound is used instead of an aldehyde, the condensation reaction occurs in toluene with toluene sulfonic acid as catalyst. For example, to prepare a specific 2-pyridinecarboxaldimine ligand, wherein R' is hydrogen, a three-component mixture is prepared. One molar equivalent of aniline, containing the desired R" substituents ($R_nC_6H_{(7-n)}N$, wherein n=1,2), is contacted with 2-pyridinecarboxaldehyde in the presence of a compound capable forming a separable azeotrope with water. Exemplary solvents include, but are not limited to, benzene and/or toluene, although, ethanol can be used, too. The mixture can be contacted, preferably refluxed, under any atmosphere to form the desired ligand. Preferably, the mixture is refluxed for at least 5 hours, or until the theoretical volume of water has been collected. The solution is then cooled and the desired ligand can be recovered. Generally, after refluxing and cooling, the ligand can be recovered as an oil or crystalline solid.

The nickel β-diketonate halide and nickel β-ketoester halide can be prepared by any method known in the art. Typical syntheses of such nickel dihalide complexes can be found in Bullen, G. J., Mason, R., and Pauling, P., *Inorganic Chemistry*, Vol. 4, pp. 456–462 (1965), herein incorporated by reference. Alternatively, and especially in the case of nickel β-diketonate halides and nickel β-ketoester halides, the salt of the β-diketone or β-ketoester can be prepared then reacted with the correct quantity of nickel halide. A mixture of an appropriate Brönsted base, such as but not limited to sodium hydride or potassium hydride or sodium methoxide or potassium methoxide, is mixed with a solvent capable of dissolving or becoming miscible with the β-diketone or β-ketoester. Exemplary solvents include toluene, benzene, methanol, or ethanol. One molar equivalent of the β-diketone or β-ketoester is added slowly to this mixture. Reaction is known to occur as evidenced by the evolution of heat and a change in the physical appearance of the mixture. Once all reactants have contacted, reaction times from 4 to 12 hours are sufficient to ensure complete reaction. If the product salt of the β-diketone or β-ketoester is not soluble in the solvent chosen, the solvent is removed by filtration or vacuum and the salt dissolved in a solvent in which it is soluble. Exemplary solvents include methanol and ethanol. This solution is then added to a one half molar equivalent of nickel halide that has been suspended or dissolved in the same solvent or a solvent with which the first solvent is miscible. The preceding reactant ratio results in the formation of the nickel bis(β-diketonate) or nickel bis(β-ketoester). If the nickel β-diketonate halide or nickel β-ketoester halide are desired, the solution is added to one molar equivalent of nickel halide as described. Reaction is known to occur as evidenced by the formation of a soluble green species. Reaction times of 4 to 12 hours are sufficient to ensure complete reaction. The byproduct sodium halide or potassium halide salt is then removed from the reaction product by filtration and/or centrifugation. The solvent is removed by vacuum to yield the nickel complex used in the 2-pyridinecarboxaldimine nickel dihalide complex synthesis.

After formation of a 2-pyridinecarboxaldimine nickel dihalide complex, the 2-pyridinecarboxaldimine nickel dihalide complex can be recovered by any method known in the art such as, for example evaporation and/or vacuum filtration of the solvent. Further, if desired, the 2-pyridinecarboxaldimine nickel dihalide complex can be further purified by washing. One exemplary wash compound can be heptane. The 2-pyridinecarboxaldimine nickel dihalide complex catalyst system can be recovered and used as a solid, heterogeneous catalyst system.

Cocatalyst Systems

Any cocatalyst system useful with 2-pyridinecarboxaldimine nickel dihalide complexes can be used. Preferably, the cocatalyst system comprises an organoaluminum compound. Most preferably, the cocatalyst system is an organoaluminum compound selected from the group consisting of methylaluminoxanes; supported, partially hydrated alkyl aluminum compounds and mixtures thereof.

When methylaluminoxane (MAO) is the cocatalyst system, any form of the methylaluminoxane can be used. Exemplary forms of MAO include, but are not limited to, a solid, a liquid, or a modification of solid forms or liquid forms of MAO.

When a supported, partially hydrated alkyl aluminum compound is used as a cocatalyst system, the support can be any known support. A solid, i.e., supported, cocatalyst can be prepared by reacting a suitable support base with an organoaluminum compound and then reacting that product with an activity promoting amount of water. The solid cocatalyst can be combined with a polymerization catalyst to form a catalyst system useful for the oligomerization or polymerization of olefins.

A wide range of materials can be used as the support base. Generally, any material that can result in a solid cocatalyst that remains insoluble in the polymerization diluent during the polymerization process can be employed as the support base. Thus, the support base includes materials that form solids when reacted with an organoaluminum compound and water as well as solids that are insoluble in the particular liquid diluent that is present during the polymerization. It is generally preferred that the support base be capable of yielding a particulate, solid cocatalyst. The support base can be a material having surface groups which are known to react with organoaluminum compounds or a material which is free of surface groups which react with organoaluminum compounds. Some examples of materials envisioned for use as a support base include, but are not limited to, starch, lignin, cellulose, sugar, silica, alumina, silica-alumina, titania, zirconia, zeolites of silica and/or alumina, magnesia, calcium carbonate, aluminum trifluoride, boron oxide, magnesium dichloride, boric acid, activated carbon, carbon black, organoboranes, organoboroxines, $Si(OMe)_3Me$, hydrocarbyl polyalcohols, boric acid, alumina, polyethylene, polyethylene glycol, and mixtures thereof.

The term organoaluminum, or alkylaluminum, compound as used herein refers to compounds of the formula $R_nAlX_{3-n}$ wherein n is a number in a range of 1 to 3, each R is the same or different organo radical, preferably a hydrocarbyl radical, and each X is a halide. Typically, each organo radical has from 1 to about 12 carbon atoms, more preferably 1 to 5 carbon atoms. Some examples of organoaluminum compounds include trialkylaluminum compounds, triarylaluminum compounds, dialkylaluminum hydrides, diarylaluminum hydrides, aryl alkyl aluminum hydrides, dialkylaluminum halides, alkyl aluminum dihalides, alkyl aluminum sesquihalides, and mixtures thereof. Some specific examples of such organoaluminum compounds include trimethylaluminum, triethylaluminum, dimethylaluminum chloride, triisopropylaluminum, triisobutylaluminum, trihexylaluminum, diethylaluminum chloride, ethyl aluminum dichloride, ethyl aluminum sesquichloride, dimethyl aluminum chloride, and mixtures thereof. Currently preferred organoaluminum compounds are alkyl aluminum compounds, especially trialkyl aluminum compounds. It is also within the scope of the present invention to use mixtures of such organoaluminum compounds.

Reactants, Polymerization and Polymer Products

As used throughout this disclosure, the terms "homopolymer", "polymer" and "copolymer" include the term "oligomer", in that the distinction between an oligomer and a polymer is difficult to ascertain; an oligomer can be considered a low molecular weight polymer. Further, oligomers produced in accordance with this invention can be prepared from one or more mono-1-olefins, as discussed for homopolymers and copolymers.

Polymers produced according to the process of this invention can be homopolymers of mono-1-olefins or copolymers of at least two different mono-1-olefins. Exemplary mono-1-olefins useful in the practice of this invention include, but are not limited to mono-1-olefins having from about 2 to about 10 carbon atoms per molecule. Preferred mono-1-olefins include, but are not limited to ethylene, propylene, 1-butene, 1-pentene, 1-hexene, 1-heptene, 3-methyl-1-butene, 4-methyl-1-pentene, 1-octene, 1-nonene and 1-decene. If the reaction product is a copolymer, one mono-1-olefin monomer can be polymerized with a mono-1 -olefin comonomer which is a different alpha-olefin, usually having from about 3 to about 10, preferably from 3 to 8 carbon atoms per molecule. Exemplary comonomers include, but are not limited to, propylene, 1-butene, 1-pentene, 1-hexene, 1-octene, 4-methyl-1-pentene, and mixtures thereof. Preferably, if the monomer is ethylene, the comonomer is 1-hexene and/or 4-methyl-1-pentene, in order to achieve maximum polymer product toughness. Preferably, if the monomer is propylene, the comonomer is ethylene and/or butene in order to achieve maximum polymer product toughness and clarity.

If a comonomer is used, the comonomer can be added to the polymerization reactor, or reaction zone, in an amount within a range of about 1 to about 20 weight percent, preferably within 7 to about 18 weight percent, based on the weight of the ethylene monomer. Most preferably, a comonomer is present in the reaction zone within a range of about 10 to about 16 weight percent, in order to produce a polymer having the most desired physical properties.

Polymerization of the monomer and optional comonomer must be carried out under slurry, also known as loop/slurry or particle form, polymerization conditions wherein the temperature is kept below the temperature at which polymer swells significantly. Slurry polymerization processes are much easier to operate and maintain than other polymerization processes; a polymer product produced by a slurry process can be recovered much more easily. Such polymerization techniques are well-known in the art and are disclosed, for instance, in Norwood, U.S. Pat. No. 3,248,179, the disclosure of which is hereby incorporated by reference.

The slurry process generally is carried out in an inert diluent (medium), such as, for example, a paraffin, cycloparaffin, and/or aromatic hydrocarbon. Preferably, the inert diluent is an alkane having less that about 12 carbon atoms per molecule, for best reactor operation and polymer product. Exemplary diluents include, but are not limited to propane, n-butane, isobutane, n-pentane, 2-methylbutane (isopentane), and mixtures thereof. Isobutane is the most preferred diluent due to low cost and ease of use.

The temperature of the polymerization reactor, or reaction zone, When using isobutane as the reactor diluent, according to this invention, is critical and must be kept within a range of about 5° to about 100° C. (41°–212° F.) and preferably within a range of about 10° to about 70° C. (50°–158° F.). Most preferably, the reaction zone temperature is within a range of 20° to 60° C. (68°–140° F.) for best catalyst activity and productivity. Reaction temperatures below about 10° C. can be ineffective for polymerization.

Pressures in the slurry process can vary from about 100 to about 1000 psia (0.76–7.6 MPa), preferably from about 200 to about 700 psia. Most preferably, the reaction zone is maintained at a pressure within a range of 300 to 600 psia for best reactor operating parameters and best resultant polymer product. The catalyst system is kept in suspension and is contacted with the monomer and comonomer(s) at sufficient pressure to maintain the medium and at least a portion of the monomer and comonomer(s) in the liquid phase. The medium and temperature are thus selected such that the polymer or copolymer is produced as solid particles and is recovered in that form. Catalyst system concentrations in the reactor can be such that the catalyst system content ranges from 0.001 to about 1 weight percent based on the weight of the reactor contents.

The catalyst system and cocatalyst system can be added to the reactor in any order to effect polymerization. For example, catalyst system can be added, then some reactor diluent, such as isobutane, followed by cocatalyst system, then more diluent and finally, monomer and optional comonomer. However, as stated earlier, this addition order can be varied, depending on equipment availability and/or desired polymer product properties. Preferably, the catalyst system and cocatalyst system are not precontacted prior to addition to the polymerization reactor due to a possible decrease in catalyst activity.

The amount of catalyst system and cocatalyst system added to the reactor can vary. Generally, a molar excess of aluminum compound is present, relative to the 2-pyridinecarboxaldimine nickel dihalide complex. Preferably, the aluminum to nickel (Al:Ni) molar ratio is less than about 5000:1, more preferably within a range of about 50:1 to about 4000:1. Most preferably, the molar ratio of aluminum to nickel is within a ratio of 100:1 to 3000:1 for best catalyst system activity and productivity.

Two preferred polymerization methods for the slurry process are those employing a loop reactor of the type disclosed in Norwood and those utilizing a plurality of stirred reactors either in series, parallel or combinations thereof wherein the reaction conditions can be the same or different in the different reactors. For instance, in a series of reactors, a chromium catalyst system which has not been subjected to the reduction step can be utilized either before or after the reactor utilizing the catalyst system of this invention.

Polymers produced in accordance with this invention generally have low molecular weights ($M_n$), as determined by intrinsic viscosity. Polymers produced in accordance with this invention also have some branching off the backbone. Usually, there are less than about 500 branches per 1000 backbone carbon atoms. Preferably, there are between about 10 and 300, most preferably between 25 and 250, branches per 100 backbone carbon atoms.

If desired, optional addition of one or more comonomers can be added to the polymerization reactor. The affirmatively added comonomers can increase the amount of short chain branching in the resultant polymer, or copolymer.

A further understanding of the invention and its advantages is provided by the following examples.

EXAMPLES

The following Examples illustrate various aspects of the invention. Data are included for each example about polymerization conditions, as well as the resultant polymer. All chemical handling, including reactions, preparation and storage, was performed under a dry, inert atmosphere (usually nitrogen). In general, catalyst systems used for polymerization in the Examples were prepared as described in this application.

The abbreviations for the catalyst systems used are as follows:

[(Me$_2$Ph)pyH]NiBr$_2$:

N-(2,6-dimethylphenyl)pyridine-2-carboxaldimine nickel (II) bromide

[(Me$_2$Ph)-6-MepyH]NiBr$_2$:

N-(2,6-dimethylphenyl)-6-methylpyridine-2-carboxaldimine nickel (II) bromide

[($^i$Pr$_2$Ph)pyH]NiBr$_2$:

N-(2,6-diisopropylphenyl)pyridine-2-carboxaldimine nickel (II) bromide

[($^i$Pr$_2$Ph)-6-MepyH]NiBr$_2$:

N-(2,6-diisopropylphenyl)-6-methylpyridine-2-carboxaldimine nickel (II) bromide

Polymer density was determined in grams per cubic centimeter (g/cc) on a compression molded sample, cooled at about 15° C. per hour, and conditioned for about 40 hours at room temperature in accordance with ASTM D1505 and ASTM D1928, procedure C. Size exclusion chromatography (SEC) analyses were performed at 140° C. on a Waters, model 150 GPC with a refractive index detector. A solution concentration of 0.17 to 0.65 weight percent in 1,2,4-trichlorobenzene was found to give reasonable elution times.

Example 1

Bench scale polymerizations for Example 1 were completed in a 380 ml pressure Schlenk tube at 5.0 bar (70 psig) ethylene pressure. Hydrogen was not charged to the reactor. The desired quantity of methylaluminoxane (MAO) (30 weight % in toluene) was charged directly to the reactor via syringe in order to achieve a Al:Ni molar ratio of 2500:1. Run time for each polymerization reaction was 5 minutes.

This example shows that not all catalyst systems are active for mono-1-olefin polymerization or oligomerization. Polymerization results are listed below in Table 1.

TABLE 1

| Run | Catalyst | Activity (g PE/g Ni · hr) |
|---|---|---|
| 101 | [(Me$_2$Ph)pyH]Ni(Br)$_2$ | 0 |
| 102 | [(Me$_2$Ph)pyMe]Ni(Br)$_2$ | 1100 |

The data in Table 1 show that 2-pyridine-carboxaldimine nickel dihalide complex/MAO catalyst systems can oligomerize or polymerize ethylene at high Al:Ni molar ratios.

Example 2

Bench scale polymerizations for Example 2 were completed in a 1 liter bench scale reactor at 70° C. at 10.0 bar (140 psig) ethylene pressure. 500 ml of ethylene was used. Hydrogen was not charged to the reactor. The cocatalyst system either was silica gel-PHT or MAO. Silica gel-PHT is partially hydrated trimethyl aluminum supported on silica gel. If silica gel-PHT was used, the desired quantity of silica gel-PHT (in toluene) was charged directly to the reactor via syringe in order to result in a Al:Ni molar ratio of 260:1. If MAO was used, the desired quantity of MAO (30 weight % in toluene) was charged directly to the reactor via syringe in order to result in a Al:Ni molar ratio of 2600:1. In all reactions, 1.0 ml of triisobutylaluminum (TIBA) (1.6M in n-hexane) was added to the reactor. Run time for each polymerization reaction, unless otherwise specified, was 5 minutes. Branching was determined using $^1$H- and $^{13}$C-NMR spectroscopy, as taught in Usami, T., *Macromolecules* Vol. 17, p. 1756 (1984) and Axelson, D., Levy, G., and Mandlekern, L., *Macromolecules* Vol. 12, p. 41 (1979), both herein incorporated by reference. Molecular weights for Runs 201 and 202 were determined using intrinsic viscosity. Molecular weights for Runs 203 and 204 were determined using GC-MS. The results are listed below in Table 2.

This example shows that oligomers and polymers can be produced using catalyst systems of the invention.

TABLE 2

| Run | Catalyst | Co-catalyst System | Activity, (g PE/g Ni · hr) | M$_n$ | Branches per 1000 carbon atoms |
|---|---|---|---|---|---|
| 211 | [($^i$Pr$_2$Ph)pyH]Ni(Br)$_2$ | Silica gel-PHT | 1300 | 20,000 | 87 |
| 212 | [($^i$Pr$_2$Ph)pyMe]Ni(Br)$_2$ | Silica gel-PHT | 1100 | 21,000 | 103 |
| 213 | [($^i$Pr$_2$Ph)pyH]Ni(Br)$_2$ | MAO | 2100 | oligomers | 116 |
| 214 | [($^i$Pr$_2$Ph)pyMe]Ni(Br)$_2$ | MAO | 2 | oligomers | 237 |

Run 214 appears to be an anomoly in that the activity is very low. Several errors could have caused this result, such as, for example, incomplete recovery of all oligomeric products and/or contamination of reactor contents. However, the data in this example show that products made from 2-pyridine-carboxaldimine nickel dihalide complex/silica gel-PHT catalyst systems have a much higher intrinsic viscosity than those produced with 2-pyridine-carboxaldimine nickel dihalide complex/MAO catalyst systems. The data in this example also show that oligomers can be prepared using 2-pyridine-carboxaldimine nickel dihalide complex/MAO catalyst systems.

While this invention has been described in detail for the purpose of illustration, it is not to be construed as limited thereby but is intended to cover all changes and modifications within the spirit and scope thereof.

That which is claimed is:

1. An oligomerization process comprising contacting in a reaction zone under slurry polymerization reactor conditions:

a) ethylene;

b) a catalyst system comprising 2-pyridine carboxaldimine nickel dihalide complex represented by the formula

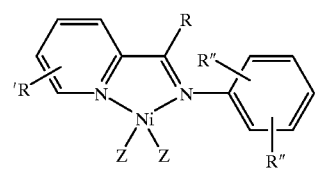

wherein R can be the same or different and is selected from the group consisting of branched and/or linear alkyl or aromatic groups having from about 1 to about 70 carbon atoms per alkyl group and can be in any position on the aromatic ring;

R' and R" on the aromatic and pyridine rings of the 2-pyridine carboxaldimine nickel dihalide complex can be the same or different, and are selected from the group consisting of hydrogen and branched or linear, aliphatic or aromatic groups having from about 1 to about 15 carbon atoms per alkyl group; and Z is a halogen selected from the group consisting of fluorine, chlorine, bromine, iodine, and mixtures thereof; and c) an organoalumium cocatalyst system;

wherein an oligomer is recovered.

2. A process according to claim 1 further comprising a comonomer selected from the group of alpha-olefins having from 3 to 10 carbon atoms per molecule is present.

3. A process according to claim 2 wherein said comonomer is selected from the group consisting of propylene, 1-butene, 1-pentene, 1-hexene, 1-octene, 4-methyl-1-pentene, and mixtures thereof.

4. A process according to claim 1 wherein said R substituent group is selected from the group consisting of hydrogen and branched, linear, cyclic, aromatic or aliphatic radicals having from about 1 to about 20 carbon atoms per radical.

5. A process according to claim 4 wherein said R substituent is terminal or is linked to the pyridine group and is selected from the group consisting of hydrogen and branched, linear, cyclic, aromatic or aliphatic radicals having from about 1 to about 12 carbon atoms per radical.

6. A process according to claim 1 wherein said R' or R" substituent is selected from the group consisting of methyl, ethyl, propyl, isopropyl, butyl, isobutyl, tert-butyl, phenyl groups, fused phenyl groups (such that the pyridine group and the substituent taken together form a quinoline group), and mixtures of two or more thereof.

7. A process according to claim 6 wherein said R' or R" substituent is an electron-donating species, selected from the group consisting of linear or branched aliphatic or fused aromatic groups having from about 1 to about 15 carbon atoms per group.

8. A process according to claim 1 wherein said Z is selected from the group consisting of chlorine, bromine and mixtures thereof.

9. A process according to claim 1 wherein said 2-pyridine carboxaldimine nickel dihalide complexes and said organoaluminum cocatalyst system are present in the reactor in amounts to have an aluminum to nickel molar ratio of less than about 5000:1.

10. A process according to claim 9 where in said aluminum to nickel molar ratio is within a range of about 10:1 to about 4000:1.

11. A process according to claim 1 wherein said slurry polymerization reactor conditions comprise a temperature within a range of about 10° to about 90° C. and a pressure within a range of about 100 to about 1000 psia.

12. A process according to claim 1 wherein said slurry polymerization reactor conditions comprise a diluent of isobutane.

13. A process according to claim 1 wherein said organoaluminum cocatalyst is selected from the group consisting of methylaluminoxanes; supported, partially hydrated alkyl aluminum compounds and mixtures thereof.

14. A process according to claim 1 wherein said organoaluminum cocatalyst is a methylaluminoxane.

15. A process according to claim 1 wherein said organoaluminum cocatalyst is a supported, partially hydrated alkyl aluminum compound.

* * * * *